United States Patent

Laurent et al.

[11] 3,944,577
[45] Mar. 16, 1976

[54] NOVEL PREGNANE-21-OIC ACID DERIVATIVES

[75] Inventors: Henry Laurent; Rudolf Wiechert, both of Berlin, Germany

[73] Assignee: Schering Aktiengesellschaft, Berlin & Bergkamen, Germany

[22] Filed: Dec. 19, 1974

[21] Appl. No.: 534,482

[30] Foreign Application Priority Data
Dec. 21, 1973 Germany............................ 2365102
Aug. 27, 1974 Germany............................ 2441284
Sept. 16, 1974 Germany............................ 24446182

[52] U.S. Cl................................ 260/397.1; 424/243
[51] Int. Cl.²............................................. C07J 9/00
[58] Field of Search................................ 260/397.1; /Machine Searched Steroids

[56] References Cited
UNITED STATES PATENTS
3,828,080  8/1974  Phillipps et al. ................. 260/397.1
3,833,563  9/1974  Laurent et al. .................. 260/397.1
3,875,194  4/1975  Laurent et al. .................. 260/397.1

*Primary Examiner*—Elbert L. Roberts
*Attorney, Agent, or Firm*—Millen, Raptes & White

[57] ABSTRACT
Pregnane-21-oic acids of the formula

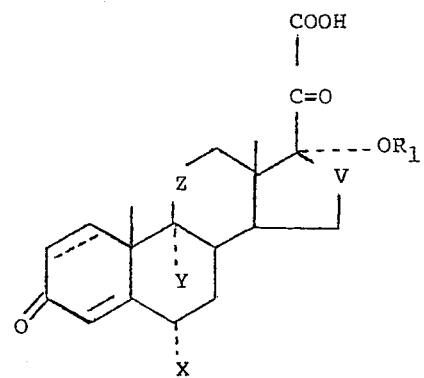

wherein X is a hydrogen atom, a fluorine atom, or methyl; Y is a hydrogen atom, a fluorine atom, or a chlorine atom; Z is methylene, carbonyl, β-hydroxymethylene, β-acyloxymethylene or when Y is a chlorine atom, β-fluoromethylene or β-chloromethylene; V is methylene, ethylidene or vinylidene; $R_1$ is a hydrogen atom or acyl, and physiologically acceptable salts thereof with bases and physiologically acceptable 21-esters thereof, possess topical anti-inflammatory activity with substantially no systemic activity.

53 Claims, No Drawings

NOVEL PREGNANE-21-OIC ACID DERIVATIVES

BACKGROUND OF THE DISCLOSURE

This invention relates to novel pharmacologically active pregnane-21-oic acid derivatives, pharmaceutical compositions comprising them and their use and to processes for the preparation thereof.

SUMMARY OF THE INVENTION

In a composition aspect, this invention relates to novel pregnane-20-oic acids and derivatives of the general formula I

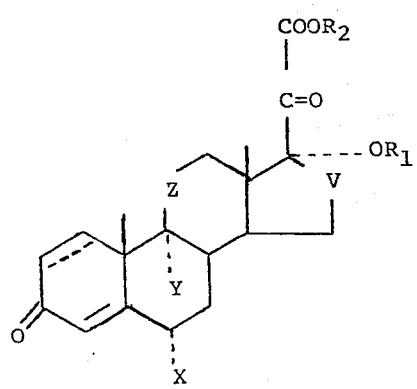

wherein X is a hydrogen atom, a fluorine atom, or methyl; Y is a hydrogen atom, a fluorine atom, or a chlorine atom; Z is methylene, carbonyl, β-hydroxymethylene, β-acyloxymethylene or when Y is a chlorine atom, β-fluoromethylene or β-chloromethylene; V is methylene ($>CH_2$), ethylidene ($>CHCH_3$) or vinylidene ($>C=CH_2$); $R_1$ is a hydrogen atom or acyl, and $R_2$ is a hydrogen atom, the cation of a physiologically acceptable base, or the residue of a physiologically acceptable alcohol, and ═══ represents a single or double bond.

In another composition aspect, this invention relates to pharmaceutical compositions comprising a compound of Formula I. In process aspects, this invention relates to processes for the production of the novel compounds of this invention and processes for their use as topical anti-inflammatory agents.

DETAILED DISCUSSION

Examples of classes of compounds of this invention embraced by Formula I are those wherein:

a. $R_1$ is H;
b. $R_1$ is α-alkanoyl of 1–8 carbon atoms;
c. ═══ is a double bond, especially those of each of (a) and (b);
d. $R_2$ is H, especially those of each of (a), (b) and (c);
e. $R_2$ is alkyl of 1–8 carbon atoms, especially those of each of (a), (b) and (c);
f. V is $>CH_2$ especially those of each of (a), (b), (c), (d) and (e).
g. V is

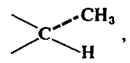

especially those of each of (a), (b), (c), (d) and (e).

h. V is

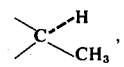

especially those of each of (a), (b), (c), (d) and (e).

i. X is H, especially those of each of (a), (b), (c), (d) (e), (f), (g) and (h).
j. X is $CH_3$, especially those of each of (a), (b), (c), (d), (e), (f), (g) and (h).
k. X is F, especially those of each of (a), (b), (c), (d), (e), (f), (g) and (h).
l. Y is H and Z is β-hydroxymethylene or carbonyl, especially those of each of (a), (b), (c), (d), (e), (f), (g), (h), (i), (j) and (k).
m. Y is Cl and F is β-hydroxymethylene or carbonyl, especially those of each of (a), (b), (c), (d), (e), (f), (g), (h), (i), (j) and (k).
n. Y and Z are Cl, especially those of (a), (b), (c), (d), (e), (f), (g), (h), (i), (j) and (k).
o. Y and Z are H, especially those of (a), (b), (c), (d), (e), (f), (g), (h), (i), (j) and (k).

Because activity resides in the pregnanoic acid steroidal structure, the 11, 17, and 21 mono- di- and tri-esters of the unesterified 11β-OH, 17α-OH and 21-COOH compounds possess the anti-inflammatory activity of the unesterified compounds.

Thus, in addition to β-hydroxymethylene, Z can be β-acyloxymethylene. When Z is β-acyloxymethylene, the acyl group is preferably that of a hydrocarbon carboxylic acid of 1–8 carbon atoms. Equivents of such esters are those of any aliphatic, cycloaliphatic, or aromatic carboxylic acid of up to 12 carbon atoms, which forms a physiologically acceptable ester of the free acids, e.g., alkanoyl of 1–8, preferably 2–6, carbon atoms, including formyl, acetyl, propionyl, butyryl, pentanoyl and hexanoyl, or the acyl radical of aromatic, carboxylic acids, preferably hydrocarbon, of 6–12 carbon atoms, e.g., benzoyl.

Similarly, in addition to being a hydrogen atom, $R_1$ can also be the acyl radical of a hydrocarbon carboxylic acid of 1–8 carbon atoms or of an equivalent acid described above.

When $R_1$ is acyl, the acyl group is preferably the same as the acyl group when Z is β-acyloxymethylene.

The 21-free acids ($R_2=H$) can form salts with alkaline metals, ammonia and amines. Included in the pregnanoic acid derivatives of this invention are the physiologically acceptable metal and ammonium salts of the free 21-acids ($R_2=$ the cation of a base, for example, an alkali metal ion, e.g., a sodium ion, a potassium ion, or an ammonium ion, e.g., ammonium, triethylammonium, pyridinium.

When $R_2$ is the radical of a physiologically acceptable alcohol, the group is preferably alkyl of 1–8 carbon atoms. Equivalents thereof are esters of other aliphatic or cycloaliphatic, saturated or unsaturated, optionally is substituted alcohol of 1–8 carbon atoms, which form physiologically acceptable 21-esters, viz., $R_2$ is an optionally substituted hydrocarbon R group.

Examples of substituents on the optionally substituted hydrocarbon R groups are: lower alkyl, e.g., methyl, ethyl, propyl, isopropyl, butyl, or tert.-butyl; aryl groups, e.g., phenyl; cycloalkyl, e.g., cyclopropyl, cyclopentyl, or cyclohexyl; hydroxy; lower alkoxy, e.g., methoxy, ethoxy, propoxy, butoxy-or tert.-butoxy; a free or esterified carboxyl group and the sodium and potassium salts thereof; amino and the acid addition salts thereof, e.g., mono- or di-lower-alkylamino, e.g., methylamino, dimethylamino, ethylamino, diethylamino, propylamino, or butylamino, and the salts thereof.

Preferred salts of the amino, mono-lower-alkylamino or di-lower-alkylamino groups are the hydrochlorides, hydrobromides, sulfates, phosphates, oxalates, maleates and tartrates.

The optionally substituted hydrocarbon R group preferably is of 1–12 carbon atoms. Specific examples of suitable R groups are: methyl, carboxymethyl, ethyl, 2-hydroxyethyl, 2-methoxyethyl, 2-aminoethyl, 2-dimethylaminoethyl, 2-carboxyethyl, propyl, allyl, cyclopropylmethyl, isopropyl, 3-hydroxypropyl, propinyl, 3-aminopropyl, butyl, sec.-butyl, tert.-butyl, 2-butyl, cyclobutyl, pentyl, isopentyl, tert.-pentyl, 2-methylbutyl, cyclopentyl, hexyl, cyclohexyl, cyclohex-2-enyl, cyclopentylmethyl, heptyl, benzyl, 2-phenylethyl, octyl, bornyl, isobornyl, menthyl, nonyl, decyl, 3-phenylpropyl, 3-phenylprop-2-enyl, dodecyl, tetradecyl, hexadecyl, and octadecyl.

In a process aspect, this invention relates to the preparation of novel pregnane-21-oic acid derivatives of general Formula I which comprises:

a. oxidizing, in an alcohol containing cyanide ions and buffered to pH 4–7 with atmospheric oxygen or with manganese (IV) oxide, a compound of general Formula II

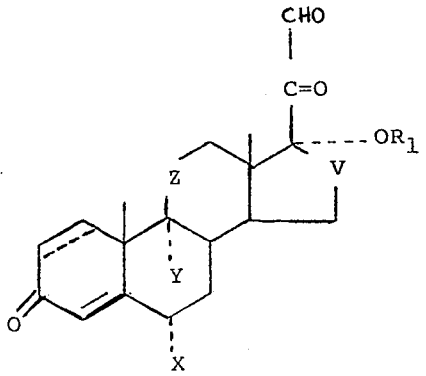

wherein $====$, X, Y, Z, V, and $R_1$ have the same values as given for Formula I, or a hydrate or hemiacetal thereof; or b. oxidizing, in an inert solvent with the amount of manganese (IV) oxide or lead (IV) oxide sufficient for the oxidation, a compound of general Formula III

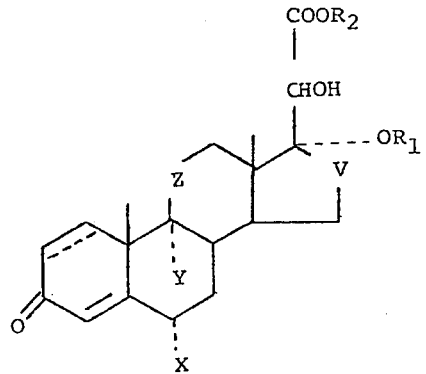

wherein $====$, X, Y, Z, V, $R_1$, and $R_2$ have the values given for Formula I; or c. conducting a conventional dehydrogenation on a compound of general Formula I wherein $====$ is a single bond, to produce a pregnane-21-oic acid derivative of general Formula I which is unsaturated in the 1-position; or d. adding hypochlorous acid, chlorine, or a mixture of fluorine and chlorine to the $\Delta^{9(11)}$-double bond of a compound of general Formula IV in a conventional manner

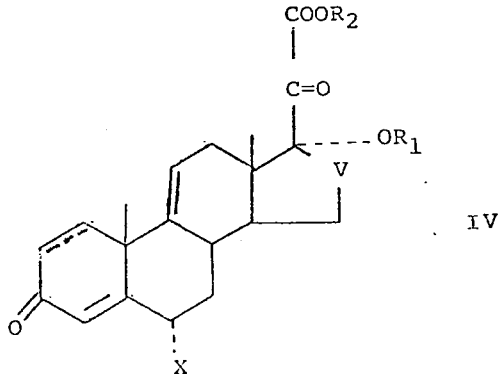

wherein $====$, X, V, $R_1$ and $R_2$ have the values given for Formula I, to produce a pregnane-21-oic acid derivative of general Formula I wherein Y is a chlorine atom, or e. opening the epoxide ring of a compound of general Formula V

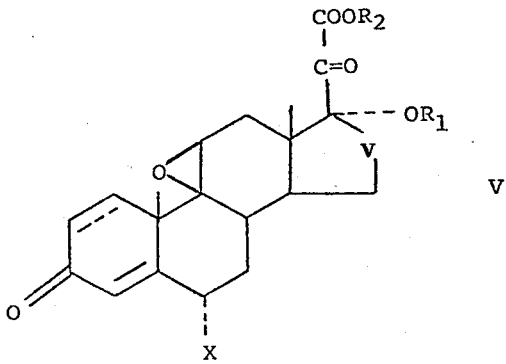

wherein $====$, X, V, $R_1$ and $R_2$ have the values given for Formula I, with hydrogen fluoride or hydrogen chloride in a conventional manner to produce a pregnane-21-oic acid derivative of Formula I wherein Y is a fluorine atom or chlorine atom and Z is a $\beta$-hydroxymethylene group.

Optionally thereafter, a hydroxy group present in the 11- position is oxidized to an 11-keto group, an ester of general Formula I is reacted in the presence of alkaline catalyst with the desired final alcohol or an ester is saponified and optionally again esterified with the desired alcohol.

The pregnanoic acid derivatives of general Formula I can be produced from compounds of general Formula II by reacting the latter in a lower alcohol with an amount, necessary for the reaction, of an oxidizing heavy metal salt, such as, for example, silver oxide, lead(IV) oxide, minium (red lead), vanadium(V) oxide, or active manganese (IV) oxide. However, the yields of desired reaction product obtained by this procedure are normally extremely unsatisfactory. Surprisingly, relatively good yields of desired products are obtained by oxidizing a compound of general Formula II or a hydrate or hemiacetal thereof, in accordance with process variant (a), with atmospheric oxygen or manganese(IV) oxide in a lower aliphatic alcohol which contains cyanide ions and has been buffered to pH 4–7.

In the process of this invention according to modification (a), active manganese(IV) oxide is used, as customarily employed for oxidation reactions. See L. F. Fieser and M. Fieser, Reagents for Organic Synthesis; John Wiley and Sons, Inc., New York, London, Sydney (1967), pp. 637 et seq.

For this variant of the process, alcohols utilized are preferably primary or secondary aliphatic or cycloaliphatic alcohols of 1–12 carbon atoms, such as, for example, methanol, ethanol, propanol, hexanol, cyclohexanol, isopropyl alcohol, butanol, butan-2-ol, pentanol, benzyl alcohol and octanol.

This reaction is conducted using cyanide ions as catalyst. Reagents yielding cyanide ions are preferably alkali metal cyanides, e.g., sodium or potassium cyanide. Preferably, 0.01 to 10 moles, especially 0.1 to 1.0 mole, of ionizable cyanide per mole of compound II are employed. If the reagents yielding cyanide ions are alkali cyanides, the reaction is conducted by adding an amount of a mineral acid, e.g., sulfuric acid, phosphoric acid, or hydrogen chloride, a sulfonic acid, e.g., p-toluenesulfonic acid, or a carboxylic acid, e.g., formic or acetic acid, required for buffering the alkali cyanide.

The process according to variant (a) is preferably accomplished in the presence of a dipolar aprotic solvent. Suitable dipolar aprotic solvents are, for example, dimethylformamide, N-methylacetamide, dimethylacetamide, N-methylpyrrolidone, dimethylsulfoxide, sulfolane, dimethylsulfone, hexamethylphosphoric triamide, and n-alkylcyanides of 1–5 carbon atoms in the alkyl residue, such as, for example, acetonitrile.

The reaction is suitably conducted by using, as the solvent, per gram of compound II, 2 ml. to 200 ml. of a mixture consisting of 5 to 50% lower alcohol and 50 to 95% of a dipolar aprotic solvent.

The reaction is advantageously carried out at a reaction temperature of from −20° C to +100°C and preferably 0° C to +50° C. The reaction time required for complete reaction depends on the reaction temperature and the selection of the reactants. For example, using atmospheric oxygen, a reaction time of 5–120 minutes is usually employed. Using active manganese(IV) oxide, a reaction time of 1–30 minutes is generally sufficient.

The starting compounds of general Formula II can be produced in a conventional manner, for example, by reacting the corresponding 21-hydroxy steroids for 20–120 minutes at room temperature with copper(II) acetate and atmospheric oxygen in a lower primary alcohol of 1–4 carbon atoms. During this reaction, mixtures of the free aldehydes and their hemiacetals are obtained which can be used without further purification as starting compounds for the process of this invention according to variant (a).

The pregnanoic acid derivatives of general Formula I can be prepared from the corresponding 20-hydroxy compounds of general Formula III by oxidizing the latter in an inert solvent with manganese (IV) oxide or lead(IV) oxide, in accordance with the process described in German Unexamined Laid-Open Application DOS No. 2,204,361 and U.S. Pat. No. 3,824,260. However, when conducting this reaction, care must be taken by means of an exact control of the reaction conditions that only the quantity of oxidizing agent required for the reaction is consumed, because the thus-formed pregnanoic acid derivatives of general Formula I, in contrast to the conventional pregnanoic acid derivatives, are in most cases of little stability under the reaction conditions utilized, and are split very easily by oxidation to compounds of general Formula VI

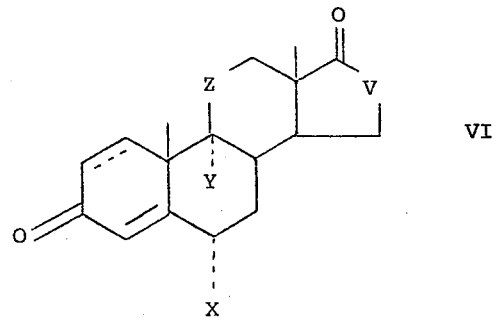

The process of this invention according to variant (b) can be conducted in the inert solvents customarily employed in the steroid chemistry for oxidation reactions. Suitable solvents are, for example, hydrocarbons, such as cyclohexane, benzene, toluene and xylene; chlorinated hydrocarbons, such as methylene chloride, chloroform, carbon tetrachloride, tetrachloroethylene and chlorobenzene; ketones, such as acetone, methyl ethyl ketone, methyl isobutyl ketone and acetophenone; and preferably ethers, such as diethyl ether, diisopropyl ether, dibutyl ether, tetrahydrofuran, dioxane and glycol dimethyl ether; or alcohols, such as methanol, ethanol, isopropanol and tert.-butanol. The process of this invention can also be conducted in mixtures of these solvents.

The process of this invention according to variant (b) can be effected using manganese(IV) oxide or lead(IV) oxide. For this modification, active manganese(IV) oxide is preferably used, as customary in steroid chemistry for oxidation reactions.

The reaction according to variant (b) is preferably accomplished at a reaction temperature of from 0° to 50° C.

To ensure that only the amount of manganese(IV) oxide or lead(IV) oxide required for the oxidation is consumed, it is advantageous to withdraw samples from the reaction mixture at various time intervals in a preliminary experiment and examine these samples analytically, for example, by means of thin-layer chromatography, to determine the optimum reaction time, which is very much dependent on the structure of the 20-hydroxy compounds employed. Normally, the optimum reaction time is 5–30 minutes when the reaction is effected at room temperature.

On the other hand, it is also possible to determine by means of preliminary tests how much lead(IV) oxide or active manganese (IV) oxide is necessary for the oxidation.

Preferred starting compounds of general Formula III are those compounds wherein the 20-hydroxy group is in the α-position. However, normally it is also possible to convert 20β-hydroxy compounds of general Formula III into the pregnanoic acid derivatives of general Formula I according to the process of this invention.

The starting materials of process variant (b) can be produced from the corresponding 20-hydroxy-20-oxopregnane derivatives. For this purpose, the latter compounds are dissolved in an alcohol, the solution is combined with copper(II) acetate, and the mixture is stirred for several days at room temperature. The mixture is then combined with aqueous ammonia; extracted with methylene chloride, for example; and the organic phase is washed with water, dried, and concentrated under vacuum. A crude product is thus obtained consisting of a mixture of the 20α- and 20β-hydroxy steroids. This mixture can be separated by dhromatography or by fractional crystallization, or it can be used without further purification as the starting substance for the process of this invention according to modification (b).

The process of this invention according to variants (c), (d), and (e), as well as the subsequent reactions which can be optionally conducted, can be carried out, for example, under the conditions described in German Unexamined Application DOS No. 2,264,003 and United States application Ser. No. 426,702, filed Dec. 20, 1973.

Examples of pregnane-20-oic acid derivatives of general Formula I which can be prepared by the process of this invention are:

11β,17α-dihydroxy-3,20-dioxo-4-pregnene-21-oic acid

11β,17α-dihydroxy-3,20-dioxo-1,4-pregnadiene-21-oic acid

9α-fluoro-11β,17α-dihydroxy-3,20-dioxo-1,4-pregnadiene-21-oic acid

6α-fluoro-11β,17α-dihydroxy-3,20-dioxo-1,4-pregnadiene-21-oic acid

9α-chloro-11β,17α-dihydroxy-3,20-dioxo-1,4-pregnadiene-21-oic acid

11β,17α-dihydroxy-3,20-dioxo-6α,16α-dimethyl-1,4-pregnadiene-21-oic acid

9α-fluoro-11β,17α-dihydroxy-3,20-dioxo-6α,16α-dimethyl-1,4-pregnadiene-21-oic acid 9α-chloro-11β,17α-dihydroxy-3,20-dioxo-6α,16α-dimethyl-1,4-pregnadiene-21-oic acid 11β,17α-dihydroxy-3,20-dioxo-16β-methyl-1,4-pregnadiene-21-oic acid 9α-fluoro-11β,17α-dihydroxy-3,20-dioxo-16β-methyl-1,4-pregnadiene-21-oic acid 9α-chloro-11β,17α-dihydroxy-3,20-dioxo-16β-methyl-1,4-pregnadiene-21-oic acid 6α-fluoro-11β,17α-dihydroxy-3,20-dioxo-16β-methyl-1,4-pregnadiene-21-oic acid 6α,9α-difluoro-11β,17α-dihydroxy-3,20-dioxo-16β-methyl-1,4-pregnadiene21-oic acid 6α-fluoro-9α-chloro-11β,17α-dihydroxy-3,20-dioxo-16β-methyl-1,4-pregnadiene-21-oic acid 11β,17α-dihydroxy-3,20-dioxo-16-methylene-1,4-pregnadiene-21-oic acid 9α-fluoro-11β,17α-dihydroxy-3,20-dioxo-16-methylene-1,4-pregnadiene-21-oic acid 9α-chloro-11β,17α-dihydroxy-3,20-dioxo-16-methylene-1,4-pregnadiene-21-oic acid 6α-fluoro-11β,17α-dihydroxy-3,20-dioxo-16-methylene-1,4-pregnadiene-21-oic acid 11β,17α-dihydroxy-3,20-dioxo-16α-methyl-1,4-pregnadiene-21-oic acid 9α-fluoro-11β,17α-dihydroxy-3,20-dioxo-16α-methyl-4-pregnene-21-oic acid 9α-fluoro-11β,17α-dihydroxy-3,20-dioxo-16α-methyl-1,4-pregnadiene-21-oic acid 6α-fluoro-11β,17α-dihydroxy-3,20-dioxo-16α-methyl-4-pregnene-21-oic acid 6α-fluoro-11β,17α-dihydroxy-3,20-dioxo-16α-methyl-1,4-pregnadiene-21-oic acid 9α-fluoro-17α-hydroxy-3,11,20-trioxo-16α-methyl-1,4-pregnadiene-21-oic acid 6α-fluoro-17α-hydroxy-3,11,20-trioxo-16α-methyl-1,4-pregnadiene-21-oic acid 17α-hydroxy-3,20-dioxo-16α-methyl-1,4-pregnadiene-21-oic acid 6α,9α-difluoro-11β,17α-dihydroxy-3,20-dioxo-16α-methyl-1,4-pregnadiene-21-oic acid 6α-fluoro-9α-chloro-11β,17α-dihydroxy-3,20-dioxo-16α-methyl-1,4-pregnadiene-21-oic acid 11β-fluoro-9α-chloro-17α-hydroxy-3,20-dioxo-16α-methyl-1,4-pregnadiene-21-oic acid 9α,11β-difluoro-17α-hydroxy-3,20-dioxo-16α-methyl-1,4-pregnadiene-21-oic acid 6α,11β-difluoro-9α-chloro-17α-hydroxy-3,20-dioxo-16α-methyl-1,4-pregnadiene-21-oic acid 6α,9α,11β-trifluoro-17α-hydroxy-3,20-dioxo-16α-methyl-1,4-pregnadiene-21-oic acid 6α,9α-difluoro-11β,17α-dihydroxy-3,20 -dioxo-16-methylene-1,4-pregnadiene-21-oic acid and 6α-fluoro-9α-chloro-11β,17α-dihydroxy-3,20-dioxo-16-methylene-1,4-pregnadiene-21-oic acid;

and the sodium salts, the methyl esters, the ethyl esters, the propyl esters, the isopropyl esters, the butyl esters, the pentyl esters, and the hexyl esters of each of these acids;

11β-hydroxy-17α-acetyloxy-3,20-dioxo-4-pregnene-21-oic acid

11β-hydroxy-17α-butyryloxy-3,20-dioxo-4-pregnene-21-oic acid

11β-hydroxy-17α-acetyloxy-3,20-dioxo-1,4-pregnadiene-21-oic acid

11β-hydroxy-17α-butyryloxy-3,20-dioxo-1,4-pregnadiene-21-oic acid

9α-fluoro-11β-hydroxy-17α-acetyloxy-3,20-dioxo-1,4-pregnadiene-21-oic acid

9α-fluoro-11β-hydroxy-17α-butyryloxy-3,20-dioxo-1,4-pregnadiene-21-oic acid

9α-fluoro-11β-hydroxy-17α-acetyloxy-3,20-dioxo-16α-methyl-1,4-pregnadiene-21-oic acid 9α-fluoro-11β-hydroxy-17α-propionyloxy-3,20-dioxo-16α-methyl-1,4-pregnadiene-21-oic acid 9α-fluoro-11β-hydroxy-17α-butyryloxy-3,20-dioxo-16α-methyl-1,4-pregnadiene-21-oic acid 9α-fluoro-11β-hydroxy-17α-acetyloxy-3,20-dioxo-16β-methyl-1,4-pregnadiene-21-oic acid 9α-fluoro-11β-hydroxy-17α-propionyloxy-3,20-dioxo-16β-methyl-1,4-pregnadiene-21-oic acid 9α-fluoro-11β-hydroxy-17α-butyryloxy-3,20-dioxo-16β-methyl-1,4-pregnadiene-21-oic acid 6α-fluoro-11β-hydroxy-17α-acetyloxy-3,20-dioxo-16α-methyl-1,4-pregnadiene-21-oic acid 6α-fluoro-11β-hydroxy-17α-butyryloxy-3,20-dioxo-16α-methyl-1,4-pregnadiene-21-oic acid 17α-acetyloxy-3,20-dioxo-4-pregnene-21-oic acid 17α-acetyloxy-3,20-dioxo-1,4-pregnadiene-21-oic acid 17α-butyryloxy-3,20-dioxo-1,4-pregnadiene-21-oic acid 17α-acetyloxy-3,11,20-trioxo-1,4-pregnadiene-21-oic acid, and 17α-butyryloxy-3,11,20-trioxo-1,4-pregnadiene-21-oic acid;

and the methyl, ethyl, aminoethyl, 2-methoxyethyl, propyl, propenyl, 2-hydroxypropyl, isopropyl, butyl, isobutyl, sec.-butyl, tert.-butyl, amyl, isoamyl, -methylbutyl, cyclopentyl, hexyl, cyclohexyl, heptyl, benzyl, menthyl, octyl, and decyl esters of each of these acids.

The compounds of general Formula I are valuable medicinal agents and intermediates for the production of medicinal agents.

The novel pregnane-21-oic acid derivatives of general Formula I are particularly distinguished by a pronounced antiinflammatory activity upon topical application, whereas they are substantially inactive systemically. Moreover, their activity has a rapid onset, a high intensity and long duration of effectiveness. They exhibit a favorable resorptive capacity and relatively good stability in galenic preparations.

The novel compounds are suitable, in combination with the carriers, pharmaceutically acceptable customary in galenic pharmacy and adapted for topical administration, for the local treatment of contact dermatitis, eczemas of a great variety of types, neurodermatoses, erythrodermia, burns, pruritus vulvae et ani, rosacea, erythematodes cutaneus, psoriasis, lichen ruber planus et verrucosus, and similar skin diseases.

These pharmaceutical compositions can be produced in the usual manner by formulating the effective agents together with a suitable additive, into the desired form of administration, such as, for example, solutions, lotions, ointments, creams and plasters. In the thus-formulated medicinal agents, the effective agent concentration is dependent on the form of application. In case of lotions and ointments, an effective agent concentration of 0.001 to 1% is preferably employed.

Moreover, the novel compounds, optionally in combination with the customary vehicles and auxiliary agents, are also well suitable for the preparation of inhalants, e.g., aerosol.

Without further elaboration, it is believed that one skilled in the art can, using the preceding desceiption, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

I SYNTHESES

EXAMPLE 1 a. 5.0 g. of 11β,17α,21-trihydroxy-1,4-pregnadiene-3,20-dione is dissolved in 500 ml. of methanol and combined with a suspension of 1.25 g. of copper(II) acetate in 500 ml. of methanol. The mixture is agitated for 2 hours at room temperature under the introduction of air, and then the mixture is diluted with methylene chloride, washed with ammonium chloride solution and water, and the organic phase is dried over sodium sulfate and concentrated under vacuum, thus obtaining 5.0 g. of 11β,17α-dihydroxy-3,20-dioxo-1,4-pregnadien-21-al as a crude product.

b. 2.8 g. of the thus-obtained aldehyde is dissolved in 90 ml. of methylene chloride and 50 ml. of methanol and mixed with 3 ml. of concentrated acetic acid and 700 mg. of potassium cyanide. The reaction mixture is stirred for 15 minutes at room temperature, then diluted with methylene chloride and washed with water. The organic phase is dried over sodium sulfate and evaporated. The residue is chromatographed on silica gel, recrystallized from acetone-hexane, and the product is 443 mg. of the methyl ester of 11β,17α-dihydroxy-3,20-dioxo-1,4-pregnadiene-21-oic acid, m.p. 215.5°.

EXAMPLE 2 a. 5.0 g. of 9α-fluoro-11β,17α,21-trihydroxy-16α-methyl-1,4-pregnadiene-3,20-dione is converted, as described in Example 1(a), into 9α-fluoro-11β,17α-dihydroxy-3,20-dioxo-16α-methyl-1,4-pregnadien-21-al.

b. 2.5 g. of the thus-obtained product is dissolved in 100 ml. of methanol. The solution is combined with 2.5 ml. of concentrated acetic acid and 400 mg. of potassium cyanide and stirred under the access of air for 25 minutes at room temperature. The mixture is then diluted with methylene chloride, washed with water, dried over sodium sulfate, and concentrated under vacuum. The crude product is chromatographed on silica gel and recrystallized from acetone-hexane, thus obtaining 719 mg. of the methyl ester of 9α-fluoro-11β,17α-dihydroxy-3,20-dioxo-16α-methyl-1,4-pregnadiene-21-oic acid, m.p. 191.6°.

EXAMPLE 3

2.5 g. of 9α-fluoro-11β,17α-dihydroxy-3,20-dioxo-16α-methyl-1,4-pregnadien-21-al is dissolved in 100 ml. of butanol, mixed with 2.5 ml. of acetic acid and 400 mg. of potassium cyanide, and agitated for 30 minutes at room temperature. The solution is diluted with methylene chloride, washed with water, dried over sodium sulfate, and concentrated by evaporation under vacuum. The crude product is chromatographed on silica gel. Recrystallization from acetone-hexane yields 67 mg. of the butyl ester of 9α-fluoro-11β,17α-dihydroxy-3,20-dioxo-16α-methyl-1,4-pregnadiene-21-oic acid, m.p. 172.8°.

EXAMPLE 4 a. 6.0 g. of 11β,17α,21-trihydroxy-4-pregnene-3,20-dione is converted, as described in Example 1(a), into 11β,17α-dihydroxy-3,20-dioxo-4-pregnen-21-al.

b. 5.0 g. of the thus-obtained product is reacted under the conditions set forth in Example 2(b). Chromatography and recrystallization from acetone-hexane yield 825 mg. of the methyl ester of 11β,17α-dihydroxy-3,20-dioxo-4-pregnene-21-oic acid, m.p. 216.6°.

EXAMPLE 5

A solution of 500 mg. of the methyl ester of 11β,17α-dihydroxy-3,20-dioxo-1,4-pregnadiene-21-oic acid in 300 ml. of butanol is cooled in an argon atmosphere to 0° and mixed with 5 ml. of a 1% solution of potassium tert.-butylate in butanol. After one minute, the mixture is acidified with 1% acetic acid and diluted with methylene chloride. The solution is washed neutral with water, dried over sodium sulfate, and concentrated under vacuum. The crude product is recrystallized from acetonehexane, thus producing 400 mg. of the butyl ester of 11β,17α-dihydroxy-3,20-dioxo-1,4-pregnadiene-21-oic acid, m.p. 153.1°.

EXAMPLE 6

300 mg. of the methyl ester of 9α-fluoro-11β,17α-dihydroxy-16α-methyl-3,20-dioxo-1,4-pregnadiene-21-oic acid is interesterified under the conditions described in Example 4, thus obtaining 121 mg. of the butyl ester of 9α-fluoro-11β,17α-dihydroxy-3,20-dioxo-16α-methyl-1,4-pregnadiene-21-oic acid, m.p. 164.5°.

EXAMPLE 7

500 mg. of the methyl ester of 11β,17α-dihydroxy-3,20-dioxo-4-pregnene-21-oic acid is converted into the butyl ester as described in Example 4. After recrystallization from methylene chloride-diisopropyl ether, 133 mg. of the butyl ester of 11β,17α-dihydroxy-3,20-dioxo-4-pregnene-21-oic acid is obtained, m.p. 119.5°.

EXAMPLE 8

250 mg. of the methyl ester of 11β,17α-dihydroxy-3,20-dioxo-4-pregnene-21-oic acid is dissolved in 50 ml. of methanol containing about 10% water. Under the exclusion of oxygen, the solution is combined with 0.5 ml. of 2N sodium hydroxide solution, and the mixture is diluted with water after 30 minutes and then extracted with methylene chloride. The aqueous phase is acidified with hydrochloric acid and thereafter extracted with diethyl ether. The ether extract is dried and evaporated under vacuum; the residue is recrystallized from methylene chloride-diisopropyl ether, thus yielding 102 mg. of 11β,17α-dihydroxy-3,20-dioxo-4-pregnene-21-oic acid, m.p. 238.5° (decomposition).

EXAMPLE 9

300 mg. of the methyl ester of 11β,17α-dihydroxy-3,20-dioxo-4-pregnene-21-oic acid is dissolved in 45 ml. of acetone. The solution is cooled to 0° and combined with 0.45 ml. of a solution containing 267 mg. of chromium(VI) oxide and 0.23 ml. of concentrated sulfuric acid per milliliter. After 5 minutes, the mixture is introduced under stirring into ice water, and the thus-obtained precipitate is filtered off. The product is dried and recrystallized from acetone-hexane, yielding 232 mg. of the methyl ester of 17α-hydroxy-3,11,20-trioxo-4-pregnene-21-oic acid, m.p. 229.7°.

EXAMPLE 10

Under the conditions indicated in Example 1, 500 mg. of 6α,9α-difluoro-11β,17α,21-trihydroxy-16α-methyl-1,4-pregnadiene-3,20-dione is converted into the methyl ester of 6α,9α-difluoro-11β,17α-dihydroxy-3,20-dioxo-16α-methyl-1,4-pregnadiene-21-oic acid.

EXAMPLE 11

Under the conditions disclosed in Example 1(a) and Example 3, 1.0 g. of 9α-fluoro-11β,17α,21-trihydroxy-16β-methyl-1,4-pregnadiene-3,20-dione is reacted, yielding after recrystallization from ether-petroleum ether 440 mg. of the butyl ester of 9α-fluoro-11β,17α-dihydroxy-3,20-dioxo-16β-methyl-1,4-pregnadiene-21-oic acid, m.p. 186.0°.

EXAMPLE 12

Under the conditions indicated in Example 1, 300 mg. of 11β,17α,21-trihydroxy-6α-methyl-1,4-pregnadiene-3,20-dione is reacted, thus obtaining 80 mg. of the methyl ester of 11β,17α-dihydroxy-3,20-dioxo-6α-methyl-1,4-pregnadiene-21-oic acid.

EXAMPLE 13

Under the conditions set forth in Example 1, 500 mg. of 9α-chloro-11β,17α,21-trihydroxy-1,4-pregnadiene-3,20-dione is converted into 138 mg. of the methyl ester of 9α-chloro-11β,17α-dihydroxy-3,20-dioxo-1,4-pregnadiene-21-oic acid.

EXAMPLE 14

Under the conditions disclosed in Example 1, 750 mg. of 11β,17α,21-trihydroxy-16-methylene-1,4-pregnadiene-3,20-dione is reacted. After recrystallization from ether-diisopropyl ether, 210 mg. of the methyl ester of 11β,17α-dihydroxy-3,20-dioxo-16-methylene-1,4-pregnadiene-21-oic acid is produced, m.p. 179°.

EXAMPLE 15 a. 20.0 g. of 11β,17α,21-trihydroxy-1,4-pregnadiene-3,20-dione is dissolved in 1 liter of methanol. The solution is combined with 10 g. of copper(II) acetate and allowed to stand for 4 weeks under access of air. Thereafter, the methanol is extensively removed under vacuum; the residue is combined with 10% strength ammonium hydroxide solution and extracted with methylene chloride. The organic phase is washed repeatedly with water, dried, and concentrated. The residue is chromatographed on silica gel. Recrystallization from acetone-hexane yields 2.40 g. of the methyl ester of 11β,17α,20ξ-trihydroxy-3-oxo-1,4-pregnadiene-21-oic acid, m.p. 254.0°.

b. 500 mg. of the methyl ester of 11β,17α,20ξ-trihydroxy-3-oxo-1,4-pregnadiene-21-oic acid is dissolved in 100 ml. of dioxane and combined with 25 g. of activated manganese(IV) oxide. The mixture is agitated for 7 minutes at room temperature, the manganese(IV) oxide is filtered off, and the filtrate is concentrated under vacuum. The residue is recrystallized from acetone-hexane, thus obtaining 218 mg. of the methyl ester of 11$\beta$,17$\alpha$-dihydroxy-3,20-dioxo-1,4-pregnadiene-21-oic acid, m.p. 206.9°.

EXAMPLE 16 a. 20.0 g. of 9$\alpha$-fluoro-11$\beta$,17$\alpha$,21-trihydroxy-16$\alpha$-methyl-1,4-pregnadiene-3,20-dione is reacted in 500 ml. of butanol with 10 g. of copper(II) acetate, as described in Example 15. The crude product is chromatographed. Recrystallization from acetone-hexane yields 1.97 g. of the butyl ester of 9$\alpha$-fluoro-11$\beta$,17$\alpha$,20$\alpha$-trihydroxy-16$\alpha$-methyl-1,4-pregnadiene-21-oic acid, m.p. 203.9°.

b. A solution of 500 mg. of the butyl ester of 9$\alpha$-fluoro-11$\beta$,17$\alpha$,20$\alpha$-trihydroxy-16$\alpha$-methyl-1,4-pregnadiene-21-oic acid in 100 ml. of dioxane is combined with 5 g. of manganese(IV) oxide and agitated for 18 hours at room temperature. The reaction mixture is filtered off from the manganese dioxide, the solvent is evaporated, and the mixture is recrystallized from acetone-hexane, thus producing 192 mg. of the butyl ester of 9$\alpha$-fluoro-11$\beta$,17$\alpha$-dihydroxy-3,20-dioxo-16$\alpha$-methyl-1,4-pregnadiene-21-oic acid, m.p. 171°.

EXAMPLE 17

Under the conditions described in Example 1, 5.0 g. of 9$\alpha$-fluoro-11$\beta$,17$\alpha$,21-trihydroxy-4-pregnene-3,20-dione is reacted, thus obtaining 688 mg. of the methyl ester of 9$\alpha$-fluoro-11$\beta$,17$\alpha$-dihydroxy-3,20-dioxo-4-pregnene-21-oic acid, m.p. 228.3° (from acetone-hexane).

EXAMPLE 18

Under the conditions set forth in Example 5, 800 mg. of the methyl ester of 9$\alpha$-fluoro-11$\beta$,17$\alpha$-dihydroxy-3,20-dioxo-4-pregnane-21-oic acid is reacted, thus obtaining 407 mg. of the butyl ester of 9$\alpha$-fluoro-11$\beta$,17$\alpha$-dihydroxy-3,20-dioxo-4-pregnene-21-oic acid, m.p. 139.7° (from acetone-hexane).

EXAMPLE 19 a. 4.0 g. of 11$\beta$,17$\alpha$,21-trihydroxy-6$\alpha$-methyl-1,4-pregnadiene-3,20-dione is dissolved in 300 ml. of methanol, combined with 1.5 g. of copper(II) acetate, and agitated for 2 hours while passing air through the mixture. The latter is combined with methylene chloride, washed with dilute ammonium chloride solution and water, dried over sodium sulfate, and evaporated under vacuum at 30°, thus obtaining 4.7 g. of 11$\beta$,17$\alpha$-dihydroxy-3,20-dioxo-6$\alpha$-methyl-1,4-pregnadien-21-al as the crude product.

b. 1.0 g. of 11$\beta$,17$\alpha$-dihydroxy-3,20-dioxo-6$\alpha$-methyl-1,4-pregnadien-21-al is dissolved under nitrogen in 25 ml. of anhydrous acetonitrile. The solution is combined with 8 ml. of absolute ethanol, 1.6 ml. of concentrated acetic acid, 2 g. of active manganese(IV) oxide, as well as 350 mg. of potassium cyanide. The mixture is stirred for 4 minutes at room temperature and then filtered off from the manganese dioxide. The filtrate is diluted with chloroform, washed with water, dried over sodium sulfate, and concentrated under vacuum. The residue is chromatographed on silica gel. With 35–60% ethyl acetate-hexane and after recrystallization from ether-hexane, 490 mg. of 11$\beta$,17$\alpha$-dihydroxy-3,20-dioxo-6$\alpha$-methyl-1,4-pregnadiene-21-oic acid ethyl ester is obtained, m.p. 205.7°.

EXAMPLE 20

1.5 g. of 11$\beta$,17$\alpha$-dihydroxy-3,20-dioxo-6$\alpha$-methyl-1,4-pregnadien-21-al is dissolved under nitrogen in 10 ml. of anhydrous methanol and 35 ml. of dimethylformamide. The mixture is combined with 2.5 ml. of concentrated acetic acid, 3 g. of active manganese(IV) oxide, and 530 mg. of potassium cyanide and agitated for 4 minutes at room temperature. The mixture is then worked up and chromatographed as described in Example 19(b). Yield: 415 mg. of the methyl ester of 11$\beta$,17$\alpha$-dihydroxy-3,20-dioxo-6$\alpha$-methyl-1,4-pregnadiene-21-oic acid, m.p. 152.4°.

EXAMPLE 21

1.3 g. of 11$\beta$,17$\alpha$-dihydroxy-3,20-dioxo-6$\alpha$-methyl-1,4-pregnadien-21-al is reacted in 25 ml. of sulfolane with 8 ml. of propanol, 1.6 ml. of acetic acid, 2 g. of manganese(IV) oxide, and 350 mg. of potassium cyanide, analogously to Example 19(b). Yield: 225 mg. of the propyl ester of 11$\beta$,17$\alpha$-dihydroxy-3,20-dioxo-6$\alpha$-methyl-1,4-pregnadiene-21-oic acid, m.p. 200.0° (from ether-hexane).

EXAMPLE 22

1.0 g. of 11$\beta$,17$\alpha$-dihydroxy-3,20-dioxo-6$\alpha$-methyl-1,4-pregnadien-21-al is reacted analogously to Example 19(b) in 25 ml. of N-methylpyrrolidone with 8 ml. of butanol, 1.6 ml. of acetic acid, 2 g. of manganese(IV) oxide, as well as 350 mg. of potassium cyanide. Yield: 487 mg. of the butyl ester of 11$\beta$,17$\alpha$-dihydroxy-3,20-dioxo-6$\alpha$-methyl-1,4-pregnadien-21-oic acid, m.p. 189.1° (from ether-hexane).

EXAMPLE 23 a. A solution of 2.5 g. of 11$\beta$,17$\alpha$,21-trihydroxy-16-methylene-1,4-pregnadiene-3,20-dione in 150 ml. of methanol is combined with 1.07 g. of copper(II) acetate and agitated for 2.5 hours at room temperature while conducting air through the mixture. The solution is then diluted with methylene chloride, washed with ammonium chloride solution and water, dried, and evaporated. The residue consists of 2.3 g. of amorphous 11$\beta$,17$\alpha$-dihydroxy-3,20-dioxo-16-methylene-1,4-pregnadien-21-al.

b. A solution of 1.0 g. of the thus-obtained aldehyde in 25 ml. of acetonitrile and 8 ml. of butanol is mixed with 1.6 ml. of concentrated acetic acid, 2 g. of active manganese(IV) oxide, and 350 mg. of potassium cyanide and agitated for 5 minutes at room temperature. The manganese dioxide is removed by filtration, and the filtrate is diluted with chloroform and washed with water. The organic phase is dried with sodium sulfate and evaporated at 50° under vacuum. The residue of 1.05 g. is chromatographed on silica gel. With 45–50% ethyl acetate-hexane and after recrystallization from ether-diisopropyl ether, 284 mg. of the butyl ester of 11$\beta$,17$\alpha$-dihydroxy-3,20-dioxo-16-methylene-1,4-pregnadiene-21-oic acid is obtained, m.p. 178.7°.

EXAMPLE 24

Under the conditions described in Example 23(b), but in the presence of propanol in place of butanol, 1.0 g. of 11$\beta$,17$\alpha$-dihydroxy-3,20-dioxo-16-methylene-1,4-pregnadien-21-al yields 286 mg. of the propyl ester of 11β,17α-dihydroxy-3,20-dioxo-16-methylene-1,4-pregnadiene-21-oic acid, m.p. 166.4° (from ether-diisopropyl ether).

EXAMPLE 25

A solution of 1.0 g. of 11β,17α-dihydroxy-3,20-dioxo-16-methylene-1,4-pregnadien-21-al in 8 ml. of ethanol and 25 ml. of hexamethylphosphoric triamide is combined with 1.6 ml. of concentrated acetic acid, 2 g. of manganese(IV) oxide, as well as 350 mg. of potassium cyanide. The mixture is stirred for 10 minutes at room temperature. The reaction product is isolated, chromatographed, and recrystallized from acetone-hexane as described in Example 23(b), yielding 400 mg. of the ethyl ester of 11β,17α-dihydroxy-3,20-dioxo-16-methylene-1,4-pregnadiene-21-oic acid, m.p. 156.7°.

EXAMPLE 26

A solution of 1.7 g. of 11β,17α-dihydroxy-3,20-dioxo-16-methylene-1,4-pregnadien-21-al in 12 ml. of methanol and 35 ml. of dimethyl sulfoxide is combined with 2.4 ml. of acetic acid, 4.5 g. of manganese(IV) oxide, as well as 530 mg. of potassium cyanide; the mixture is agitated for 3 minutes at room temperature. The reaction product is isolated, chromatographed, and recrystallized from ether-diisopropyl ether, as described in Example 23(b). Yield: 490 mg. of the methyl ester of 11β,17α-dihydroxy-3,20-dioxo-16-methylene-1,4-pregnadiene-21-oic acid, m.p. 181.4°.

EXAMPLE 27

Analogously to Example 19, but with the use of methanol in place of ethanol, the methyl ester of 6α-fluoro-11β,17α-dihydroxy-3,20-dioxo-16α-methyl-1,4-pregnadiene-21-oic acid is produced, m.p. 182.6°

EXAMPLE 28

Analogously to Example 19, the ethyl ester of 6α-fluoro-11β,17α-dihydroxy-3,20-dioxo-16α-methyl-1,4-pregnadiene-21-oic acid is prepared, m.p. 140.5°.

EXAMPLE 29

In analogy to Example 19, but using propanol instead of ethanol, the propyl ester of 6α-fluoro-11β,17α-dihydroxy-3,20-dioxo-16α-methyl-1,4-pregnadiene-21-oic acid is obtained, m.p. 134.3°.

EXAMPLE 30

Analogously to Example 19, but with butanol in place of ethanol, the butyl ester of 6α-fluoro-11β,17α-dihydroxy-3,20-dioxo-16α-methyl-1,4-pregnadiene-21-oic acid is prepared, m.p. 169.6°.

EXAMPLE 31

In analogy to Example 19, the ethyl ester of 6α-fluoro-11β,17α-dihydroxy-3,20-dioxo-1,4-pregnadiene-21-oic acid is prepared, m.p. 238.5°.

EXAMPLE 32

Analogously to Example 19, but using butanol instead of ethanol, the butyl ester of 6α-fluoro-11β,17α-dihydroxy-3,20-dioxo-1,4-pregnadiene-21-oic acid is produced, m.p. 193.4°.

EXAMPLE 33

The ethyl ester of 9α-fluoro-11β,17α-dihydroxy-3,20-dioxo-16α-methyl-1,4-pregnadiene-21-oic acid, m.p. 184.2°, is prepared analogously to Example 19.

EXAMPLE 34

In analogy to Example 19, but employing isopropyl alcohol in place of ethanol, the isopropyl ester of 9α-fluoro-11β,17α-dihydroxy-3,20-dioxo-16α-methyl-1,4-pregnadiene-21-oic acid is prepared, m.p. 174.7°.

EXAMPLE 35

Analogously to Example 19, but with pentanol instead of ethanol, the pentyl ester of 9α-fluoro-11β,17α-dihydroxy-3,20-dioxo-16α-methyl-1,4-pregnadiene-21-oic acid is obtained, m.p. 165.5°.

EXAMPLE 36

In analogy to Example 19, the ethyl ester of 11β,17α-dihydroxy-3,20-dioxo-1,4-pregnadiene-21-oic acid is produced, m.p. 225.9°.

EXAMPLE 37 a. 2.0 g. of 11β,21-dihydroxy-17α-butyryloxy-4-pregnene-3,20-dione is dissolved in 150 ml. of methanol and combined with 1.2 g. of copper(II) acetate. The solution is stirred for 2 hours while passing air therethrough. The reaction mixture is then diluted with methylene chloride, washed with ammonium chloride solution and water, dried over sodium sulfate, and concentrated under vacuum at 30°. Yield: 2.17 g. of 11β-hydroxy-17α-butyryloxy-3,20-dioxo-4-pregnen-21-al as a crude product.

b. 1.0 g. of 11β-hydroxy-17α-butyryloxy-3,20-dioxo-4-pregnen-21-al is dissolved, under a nitrogen atmosphere, in 5 ml. of absolute methanol and 30 ml. of acetonitrile. This solution is combined with 1.6 ml. of concentrated actic acid, 2 g. of manganese(IV) oxide, as well as 350 mg. of potassium cyanide; the mixture is allowed to react for 8 minutes at room temperature. The manganese dioxide is filtered off, the filtrate is diluted with chloroform, washed with water, and dried over sodium sulfate. After evaporation of the solvent, 1.25 g. of an oil is obtained which is chromatographed on silica gel. With 40–45% ethyl acetate-hexane and after recrystallization from ether-petroleum ether, 360 mg. of the methyl ester of 11β-hydroxy-17α-butyryloxy-3,20-dioxo-4-pregnene-21-oic acid is obtained, m.p. 197.7°.

EXAMPLE 38

1.0 g. of 11β-hydroxy-17α-butyryloxy-3,20-dioxo-4-pregnen-21-al is reacted in 25 ml. of acetonitrile with 8 ml. of butanol, 1.6 ml. of concentrated acetic acid, 3 g. of manganese(IV) oxide, and 350 mg. of potassium cyanide. After 10 minutes, the reaction product is isolated and chromatographed as described in Example 37(b). After recrystallization from ether-petroleum ether, 340 mg. of the butyl ester of 11β-hydroxy-17α-butyryloxy-3,20-dioxo-4-pregnene-21-oic acid is obtained, m.p. 111.7°.

EXAMPLE 39 a. A solution of 6.0 g. of 21-hydroxy-17β-acetoxy-4-pregnene-3,20-dione in 300 ml. of methanol is combined with 2.7 g. of copper(II) acetate and agitated for 1 hour at room temperature while introducing air into the mixture. The latter is then diluted with methylene chloride, washed with ammonium chloride solution and water, dried over sodium sulfate, and concentrated under vacuum. The yield is 6.7 g. of 17α-acetoxy-3,20-dioxo-4-pregnen-21-al as a crude product.

b. 2.6 g. of 17α-acetoxy-3,20-dioxo-4-pregnen-21-al is dissolved in 21 ml. of butanol and 65 ml. of dimethylformamide. The solution is subsequently mixed with 4.2 ml. of concentrated acetic acid, 7.8 g. of active manganese(IV) oxide, and 915 mg. of potassium cyanide and strongly agitated for 10 minutes at room temperature. The manganese(IV) oxide is removed by filtration; the filtrate is diluted with chloroform, washed with water, and dried with sodium sulfate. The solvent is evaporated and the residue chromatographed. With 13–19% ethyl acetatehexane, 557 mg. of an oil is obtained which is crystallized from ether-petroleum ether. Yield: 275 mg. of the butyl ester of 17α-acetoxy-3,20-dioxo-4-pregnene-21-oic acid, m.p. 139.5°.

EXAMPLE 40

4.0 g. of 17α-acetoxy-3,20-dioxo-4-pregnen-21-al is agitated at room temperature for 5 minutes in 100 ml. of N-methylpyrrolidone with 32 ml. of methanol, 6.4 ml. of concentrated acetic acid, 12 g. of manganese(IV) oxide, and 1.4 g. of potassium cyanide. The reaction product is then isolated as set forth in Example 39(b). After recrystallization from acetone-petroleum ether, 1.98 g. of the methyl ester of 17α-acetoxy-3,20-dioxo-4-pregnene-21-oic acid is obtained, m.p. 190.3°.

EXAMPLE 41

Analogously to Example 37, but with butanol in place of methanol, 11β, 21-dihyroxy-17α-propionyloxy-1,4-pregnadiene-3,20-dione is converted into the butyl ester of 11β-hydroxy-17α-propionyloxy-3,20-dioxo-1,4-pregnadiene-21-oic acid.

EXAMPLE 42

In analogy to Example 37, but using ethanol instead of methanol, 11β,21-dihydroxy-17α-propionyloxy-1,4-pregnadiene-3,20-dione is converted into the ethyl ester of 11β-hydroxy-17α-propionyloxy-3,20-dioxo-1,4-pregnadiene-21-oic acid.

EXAMPLE 43

Under the conditions described in Example 39, but with isopropyl alcohol in place of butanol, 9α-fluoro-11β,21-dihydroxy-17α-acetoxy-16α-methyl-1,4-pregnadiene-3,20-dione is converted into the isopropyl ester of 9α-fluoro-11β-hydroxy-17α-acetoxy-3,20-dioxo-16α-methyl-1,4-pregnadiene-21-oic acid.

EXAMPLE 44

Under the conditions recited in Example 39, 9α-fluoro-11β, 21-dihydroxy-17α-propionyloxy-16β-methyl-1,4-pregnadiene-3,20-dione is converted into the butyl ester of 9α-fluoro-11β-hydroxy-17α-propionyloxy-3,20-dioxo-16β-methyl-1,4-pregnadiene-21-oic acid.

EXAMPLE 45

Under the conditions described in Example 37, 9α-fluoro-11β,21-dihydroxy-17α-benzoyloxy-16β-methyl-1,4-pregnadiene-3,20-dione is converted into the methyl ester of 9α-fluoro-11β-hydroxy-17α-benzoyloxy-3,20-dioxo-16β-methyl-1,4-pregnadiene-21-oic acid.

EXAMPLE 46

Under the conditions disclosed in Example 37, but with the use of pentanol in place of methanol, 6α-fluoro-11β,21-dihydroxy-17α-butyryloxy-1,4-pregnadiene-3,20-dione is converted into the pentyl ester of 6α-fluoro-11β-hydroxy-17α-butyryloxy-3,20-dioxo-1,4-pregnadiene-21-oic acid.

EXAMPLE 47

Under the conditions set forth in Example 37, 11β,21-dihydroxy-17α-acetoxy-6α-methyl-1,4-pregnadiene-3,20-dione is converted into the methyl ester of 11β-hydroxy-17α-acetoxy-3,20-dioxo-6α-methyl-1,4-pregnadiene-21-oic acid.

EXAMPLE 48

Under the conditions described in Example 39, 6α,9α-difluoro-11β,21-dihydroxy-17α-acetoxy-16α-methyl-1,4-pregnadiene-3,20-dione is converted into the butyl ester of 6α,9α-difluoro-11β-hydroxy-17α-acetoxy-3,20-dioxo-16α-methyl-1,4-pregnadiene-21-oic acid.

EXAMPLE 49

Under the reaction conditions described in Example 37, but using propanol instead of methanol, 9α,11β-dichloro-21-hydroxy-17α-propionyloxy-1,4-pregnadiene-3,20-dione is converted into the propyl ester of 9α,11β-dichloro-17α-propionyloxy-3,20-dioxo-1,4-pregnadiene-21-oic acid.

EXAMPLE 50

Under the conditions set forth in Example 39, but with ethanol in place of butanol, 21-hydroxy-17α-propionyloxy-1,4-pregnadiene-3,11,20-trione is converted into the ethyl ester of 17α-propionyloxy-3,11,20-trioxo-1,4-pregnadiene-21-oic acid.

EXAMPLE 51

Under the conditions set forth in Example 39, 21-hydroxy-11β,17α-diacetoxy-1,4-pregnadiene-3,20-dione is converted into the butyl ester of 11β,17α-diacetoxy-3,20-dioxo-1,4-pregnadiene-21-oic acid.

II. PHARMACEUTICAL PREPARATIONS

EXAMPLE A

Composition for an Ointment:
0.01 % Butyl ester of 6α-fluoro-11β,17α-dihydroxy-3,20-dioxo-16α-methyl-1,4-pregnadiene-21-oic acid 2.50 % "Allercur" hexachlorophenate, micronized, particle size about 8 μ (Allercur = registered trademark for 1-p-chlorobenzyl-2-pyrrolidylmethylbenzimidazole)
6.00 % "Hostaphat" KW 340 (tertiary ester of o-phosphoric acid and wax alcohol tetraglycol ether)
0.10 % Sorbic acid
10.00 % Neutral oil ("Migloyol 812")
3.50 % Stearyl alcohol
1.50 % Lanolin, anhydrous DAB [German Pharmacopoeia] 6
76.39 % Desalted water

EXAMPLE B

Composition for an Ointment:
0.01 g. Butyl ester of 9α-fluoro-11β,17α-dihydroxy-3,20-dioxo-16α-methyl-1,4-pregnadiene-21-oic acid
5.00 g. White wax, DAB 6
5.00 g. Lanolin, anhydrous DAB 6
20.00 g. Vaseline, white DAB 6
25.00 g. Amphocerin K "Dehydag"
14.97 g. Paraffin oil, liquid DAB 6
30.00 g. Desalted water
0.02 g. "Crematest" perfume oil No. 6580 "Dragee"

EXAMPLE C

Composition of Eye Drops (Oily):
100 mg. of the butyl ester of 11β, 17α-dihydroxy-3,20-dioxo-1,4-pregnadiene-21-oic acid is dissolved in
100 ml. of castor oil.
After the addition of 200 mg. of chloramphenicol (or another bacteriostatic agent), the solution is filtered under sterile conditions and dispensed aseptically.

EXAMPLE D

Composition for Ear Drops
100 mg. of the propyl ester of 9α-fluoro-11β,17α-dihydroxy-3,20-dioxo-16β-methyl-1,4-pregnadiene-21-oic acid is dissolved in 1,2-propylene glycol/ethyl alcohol
(9:1). Then, 200 mg. of chloramphenicol is added to the solution which had been replenished to 100 ml.

EXAMPLE E

Production of an Inhalant:
1,000 g. of micronized butyl ester of 11β-hydroxy-17α-butyryloxy-3,20-dioxo-4-pregnene-21-oic acid (average particle size smaller than 7 μ) and
39,000 g. of ground lactose
are mixed together. Respectively 40 mg. of the mixture is filled into capsules.
The inhalant can be administered, after opening of the capsule, by breathing the mixture, preferably by sniffing. Alternatively, a "Spinhaler" is utilized for the application of the inhalant.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A pregnane-21-oic acid derivative of the formula

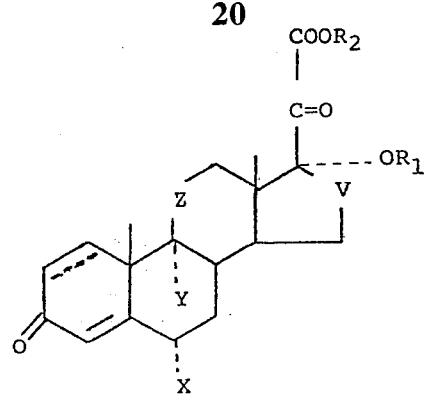

wherein X is a hydrogen atom, a fluorine atom, or methyl; Y is a hydrogen atom, a fluorine atom, or a chlorine atom; Z is methylene, carbonyl, a β-hydroxymethylene, β-acyloxymethylene whereby acyl is the acyl radical of a hydrocarbon carboxylic acid of 1–8 carbon atoms, or when Y is a chlorine atom, β-fluoromethylene or β-chloromethylene; V is $>CH_2$, $>CHCH_3$ or $>C=CH_2$; $R_1$ is a hydrogen atom or the acyl radical of a hydrocarbon carboxylic acid of 1–8 carbon atoms, and $R_2$ is a hydrogen atom or alkyl of 1–8 carbon atoms, and the bond====represents a single or double bond, and, when $R_2$ is H, the physiologically acceptable metal and ammonium salts thereof.

2. A compound of claim 1, wherein $R_2$ is alkyl of 1–8 carbon atoms.
3. A compound of claim 2, wherein $R_1$ is H.
4. A compound of claim 3, wherein Z is β-hydroxymethylene or carbonyl.
5. The compound of claim 1, the methyl ester of 11β,17α-dihydroxy-3,20-dioxo-1,4-pregnadiene-21-oic acid.
6. The compound of claim 1, the methyl ester of 9α-fluoro-11β,17α-dihydroxy-3,20-dioxo-16α-methyl-1,4-pregnadiene-21-oic acid.
7. The compound of claim 1, the butyl ester of 9α-fluoro-11β,17α-dihydroxy-3,20-dioxo-16α-methyl-1,4-pregnadiene-21-oic acid.
8. The compound of claim 1, the methyl ester of 11β,17α-dihydroxy-3,20-dioxo-4-pregnene-21-oic acid.
9. The compound of claim 1, the butyl ester of 11β,17α-dihydroxy-3,20-dioxo-1,4-pregnadiene-21-oic acid.
10. The compound of claim 1, the butyl ester of 11β,17α-dihydroxy-30,20-dioxo-4-pregnene-21-oic acid.
11. The compound of claim 1, the 11β,17α-dihydroxy-3,20-dioxo-4-pregnene-21-oic acid.
12. The compound of claim 1, the methyl ester of 17α-hydroxy-3,11,20-trioxo-4-pregnene-21-oic acid.
13. The compound of claim 1, the methyl ester of 6α,9α-difluoro-11β,17α-dihydroxy-3,20-dioxo-16α-methyl-1,4-pregnadiene-21-oic acid.
14. The compound of claim 1, the methyl ester of 9α-fluoro-11β,17α-dihydroxy-3,20-dioxo-16β-methyl-1,4-pregnadiene-21-oic acid.
15. The compound of claim 1, the methyl ester of 11β,17α-dihydroxy-3,20-dioxo-6α-methyl-1,4-pregnadiene-21-oic acid.
16. The compound of claim 1, the methyl ester of 9α-chloro-11β,17α-dihydroxy-3,20-dioxo-1,4-pregnadiene-21-oic acid.
17. The compound of claim 1, the methyl ester of 11β,17α-dihydroxy-3,20-dioxo-16-methylene-1,4-pregnadiene-21-oic acid.

18. The compound of claim 1, the methyl ester of 9α-fluoro-11β,17α-dihydroxy-3,20-dioxo-4-pregnene-21-oic acid.

19. The compound of claim 1, the butyl ester of 9α-fluoro-11β,17α-dihydroxy-3,20-dioxo-4-pregnene-21-oic acid.

20. The compound of claim 1, the ethyl ester of 11β,17α-dihydroxy-3,20-dioxo-6α-methyl-1,4-pregnadiene-21-oic acid.

21. The compound of claim 1, the propyl ester of 11β,17α-dihydroxy-3,20-dioxo-6α-methyl-1,4-pregnadiene-21-oic acid.

22. The compound of claim 1, the butyl ester of 11β,17α-dihydroxy-3,20-dioxo-6α-methyl-1,4-pregnadiene-21-oic acid.

23. The compound of claim 1, the butyl ester of 11β-17α-dihydroxy-3,20-dioxo-16-methylene-1,4-pregnadiene-21-oic acid.

24. The compound of claim 1, the propyl ester of 11β,17α-dihydroxy-3,20-dioxo-16-methylene-1,4-pregnadiene-21-oic acid.

25. The compound of claim 1, the ethyl ester of 11β,17α-dihydroxy-3,20-dioxo-16-methylene-1,4-pregnadiene-21-oic acid.

26. The compound of claim 1, the methyl ester of 6α-fluoro-11β,17α-dihydroxy-3,20-dioxo-16α-methyl-1,4-pregnadiene-21-oic acid.

27. The compound of claim 1, the ethyl ester of 6α-fluoro-11β,17α-dihydroxy-3,20-dioxo-16α-methyl-1,4-pregnadiene-21-oic acid.

28. The compound of claim 1, the propyl ester of 6α-fluoro-11β,17α-dihydroxy-3,20-dioxo-16α-methyl-1,4-pregnadiene-21-oic acid.

29. The compound of claim 1, the butyl ester of 6α-fluoro-11β,17α-dihydroxy-3,20-dioxo-16α-methyl-1,4-pregnadiene-21-oic acid.

30. The compound of claim 1, the ethyl ester of 6α-fluoro-11β,17α-dihydroxy-3,20-dioxo-1,4-pregnadiene-21-oic acid.

31. The compound of claim 1, the butyl ester of 6α-fluoro-11β,17α-dihydroxy-3,20-dioxo-1,4-pregnadiene-21-oic acid.

32. The compound of claim 1, the ethyl ester of 9α-fluoro-11β,17α-dihydroxy-3,20-dioxo-16α-methyl-1,4-pregnadiene-21-oic acid.

33. The compound of claim 1, the isopropyl ester of 9α-fluoro-11β,17α-dihydroxy-3,20-dioxo-16α-methyl-1,4-pregnadiene-21-oic acid.

34. The compound of claim 1, the pentyl ester of 9α-fluoro-11β,17α-dihydroxy-3,20-dioxo-16α-methyl-1,4-pregnadiene-21-oic acid.

35. The compound of claim 1, the ethyl ester of 11β,17α-dihydroxy-3,20-dioxo-1,4-pregnadiene-21-oic acid.

36. The compound of claim 1, the butyl ester of 11β-hydroxy-17α-butyryloxy-3,20-dioxo-4-pregnene-21-oic acid.

37. The compound of claim 1, the methyl ester of 11β-hydroxy-17α-butyryloxy-3,20-dioxo-4-pregnene-21-oic acid.

38. The compound of claim 1, the butyl ester of 17α-acetoxy-3,20-dioxo-4-pregnene-21-oic acid.

39. The compound of claim 1, the methyl ester of 17α-acetoxy-3,20-dioxo-4-pregnene-21-oic acid.

40. The compound of claim 1, the butyl ester of 11β-hydroxy-17α-propionyloxy-3,20-dioxo-1,4-pregnadiene-21-oic acid.

41. The compound of claim 1, the ethyl ester of 11β-hydroxy-17α-propionyloxy-3,20-dioxo-1,4-pregnadiene-21-oic acid.

42. The compound of claim 1, the isopropyl ester of 9α-fluoro-11β-hydroxy-17α-acetoxy-3,20-dioxo-16α-methyl-1,4-pregnadiene-21-oic acid.

43. The compound of claim 1, the butyl ester of 9α-fluoro-11β-hydroxy-17α-propionyloxy-3,20-dioxo-16β-methyl-1,4-pregnadiene-21-oic acid.

44. The compound of claim 1, the methyl ester of 9α-fluoro-11β-hydroxy-17α-benzoyloxy-3,20-dioxo-16β-methyl-1,4-pregnadiene-21-oic acid.

45. The compound of claim 1, the pentyl ester of 6α-fluoro-11β-hydroxy-17α-butyryloxy-3,20-dioxo-1,4-pregnadiene-21-oic acid.

46. The compound of claim 1, the methyl ester of 11β-hydroxy-17α-acetoxy-3,20-dioxo-6α-methyl-1,4-pregnadiene-21-oic acid.

47. The compound of claim 1, the butyl ester of 6α,9α-difluoro-11β-hydroxy-17α-acetoxy-3,20-dioxo-16α-methyl-1,4-pregnadiene-21-oic acid.

48. The compound of claim 1, the propyl ester of 9α,11β-dichloro-17α-propionyloxy-3,20-dioxo-1,4-pregnadiene-21-oic acid.

49. The compound of claim 1, the ethyl ester of 17α-propionyloxy-3,11,20-trioxo-1,4-pregnadiene-21-oic acid.

50. The compound of claim 1, the butyl ester of 11β,17α-diacetoxy-3,20-dioxo-1,4-pregnadiene-21-oic acid.

51. A pharmaceutical composition adapted for topical administration comprising an anti-inflammatorily effective concentration therein of a compound of claim 1, in admixture with a pharmaceutically acceptable carrier adapted for topical administration.

52. A method for the treatment of an inflammatory condition of the skin which comprises applying topically to the inflamed area an anti-inflammatorily effective amount of a composition of claim 51.

53. A process for the production of a pregnane-21-oic acid or derivative thereof of claim 1, which comprises oxidizing a compound of the formula

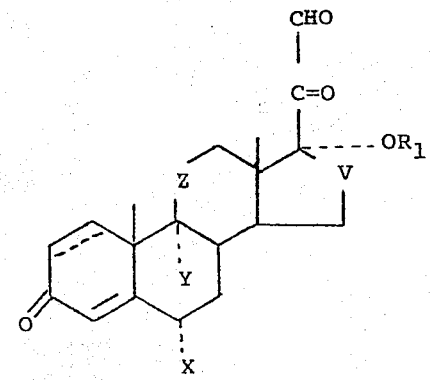

wherein ===X, Y, Z. V, and R₁ have the values given therein or a hydrate or hemiacetal thereof, with atmospheric oxygen or with manganese(IV) oxide, in an alcohol containing cyanide ions and buffered to pH 4–7.

* * * * *